US008033286B2

(12) United States Patent
Perry

(10) Patent No.: US 8,033,286 B2
(45) Date of Patent: Oct. 11, 2011

(54) HAIR TREATMENT DEVICE

(75) Inventor: Jeffrey Wayne Perry, Grand Island, NE (US)

(73) Assignee: JProducts, Inc., Alda, NE (US)

( * ) Notice: Subject to any disclaimer, the term of this patent is extended or adjusted under 35 U.S.C. 154(b) by 551 days.

(21) Appl. No.: 12/041,136

(22) Filed: Mar. 3, 2008

(65) Prior Publication Data

US 2008/0257370 A1 Oct. 23, 2008

(51) Int. Cl.
*A45D 19/18* (2006.01)
*A61K 8/18* (2006.01)
*A46B 11/00* (2006.01)

(52) U.S. Cl. .......................... 132/270; 132/208; 401/10

(58) Field of Classification Search .................. 132/200, 132/202, 203, 205, 207, 208, 209, 234, 244, 132/270, 221, 222, 108–112; 401/9, 10, 401/207, 196, 203, 261
See application file for complete search history.

(56) References Cited

U.S. PATENT DOCUMENTS 3,692,032 A 9/1972 Regas
4,108,184 A 8/1978 Morganroth
4,144,897 A 3/1979 Mosz
4,398,549 A 8/1983 Thomas
4,398,893 A 8/1983 Johns
4,503,870 A 3/1985 Peterson
4,552,159 A 11/1985 Fabbri et al.
4,942,893 A 7/1990 Trottier
5,042,514 A 8/1991 Bastien
5,146,937 A 9/1992 Lefebvre
5,156,172 A * 10/1992 Tancredi ........................ 132/270
5,287,864 A 2/1994 Gallo
5,469,873 A 11/1995 Guth
5,535,764 A 7/1996 Abramson
5,664,590 A 9/1997 Plateroti et al.
5,706,839 A * 1/1998 Patti .............................. 132/277
5,899,213 A * 5/1999 Kimata .......................... 132/225
6,209,549 B1 * 4/2001 Lunde ........................... 132/207
6,626,699 B1 9/2003 Epe et al.
6,748,957 B1 6/2004 Giordano
(Continued)

FOREIGN PATENT DOCUMENTS

DE 296 16 331 11/1996
(Continued)

OTHER PUBLICATIONS

International Search Report and Written Opinion dated Mar. 17, 2009 for Application No. PCT/US2008/082432.

*Primary Examiner* — Todd Manahan
*Assistant Examiner* — Vanitha Elgart
(74) *Attorney, Agent, or Firm* — Frost Brown Todd LLC

(57) ABSTRACT

Disclosed herein is device where one embodiment is for use in chemically treating hair, particularly highlighting or coloring hair. One embodiment of the device may be reusable, recyclable, and transparent. Another embodiment of the device may comprise lightweight panels, at least a portion of which is transparent such that the stylist is able to view the results of the treatment process without opening the device. One embodiment of the device may be quickly and easily applied to and removed from the hair. Another embodiment of the device may be easily produced where all components of the device are integrally manufactured. An embodiment may also be adapted to comprise at least two compartments, such that multiple different chemical products may be simultaneously applied, while still retaining the benefits and advantages of the device.

17 Claims, 12 Drawing Sheets

U.S. PATENT DOCUMENTS

| | | | | |
|---|---|---|---|---|
| 7,543,591 | B1 * | 6/2009 | Munsil | 132/270 |
| 2004/0129290 | A1 | 7/2004 | Kwan | |
| 2005/0039768 | A1 | 2/2005 | Winckels | |
| 2006/0130867 | A1 | 6/2006 | Bird | |
| 2006/0272665 | A1 * | 12/2006 | Yamamoto et al. | 132/207 |
| 2008/0083418 | A1 * | 4/2008 | Glenn et al. | 132/208 |
| 2009/0084393 | A1 * | 4/2009 | Baker et al. | 132/208 |
| 2009/0084394 | A1 * | 4/2009 | Baker et al. | 132/208 |
| 2010/0101595 | A1 * | 4/2010 | Glenn et al. | 132/208 |

FOREIGN PATENT DOCUMENTS

| | | |
|---|---|---|
| EP | 1 897 459 | 3/2008 |
| EP | 1 915 920 | 4/2008 |
| GB | 2 419 288 | 4/2006 |

* cited by examiner

HAIR TREATMENT DEVICE

BACKGROUND OF THE INVENTION

This invention relates generally to methods of chemically treating hair, and devices suitable for such use.

BRIEF DESCRIPTION OF THE DRAWING

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
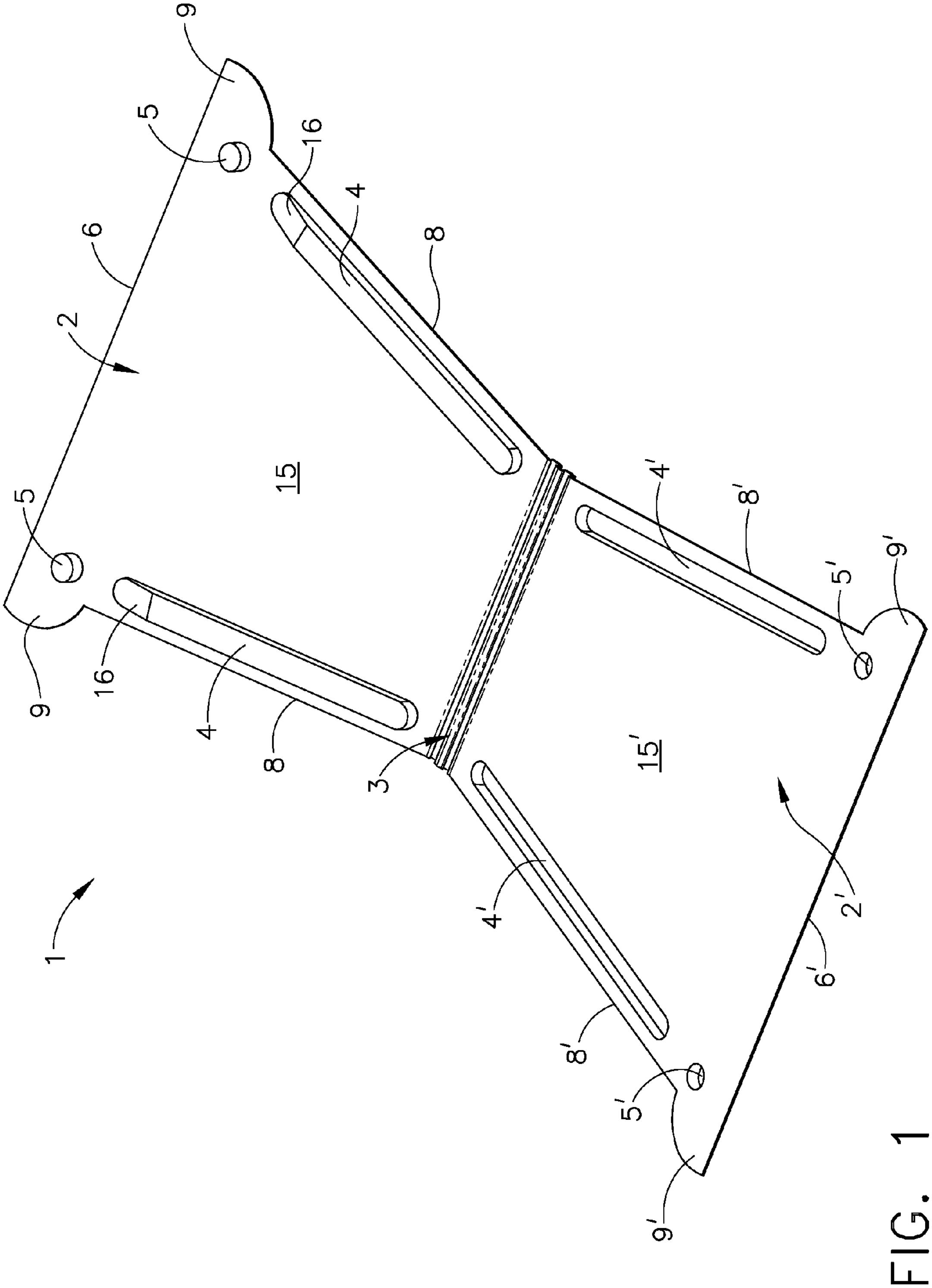
FIG. 1 depicts a perspective view of one embodiment of a hair treatment device.

Reference will now be made in detail to the present preferred embodiment of the invention, an example of which is illustrated in the accompanying drawings.

DETAILED DESCRIPTION

In the following description, like reference characters designate like or corresponding parts throughout the several views. Also, in the following description, it is to be understood that terms such as front, back, inside, outside, and the like are words of convenience and are not to be construed as limiting terms. Terminology used in this patent is not meant to be limiting insofar as devices described herein, or portions thereof, may be attached or utilized in other orientations. Referring in more detail to the drawings, an embodiment of the invention will now be described.

FIGS. 1-13 depict embodiments of a hair treatment device. As depicted in FIGS. 1-7, a hair treatment device 1 comprises a first and a second panel, 2, 2', joined by a hinge 3. As further depicted in FIGS. 1-7, panels 2, 2' respectively comprise a proximal end 7, 7' adjacent hinge 3 and a distal end 6, 6' opposite hinge 3. The panels 2, 2' as depicted in FIGS. 1-8, comprise a plurality of barriers 4, 4' and a plurality of fasteners 5, 5'.

The barriers 4, 4' of device 1 respectively define at least one receiving well 15, 15' on the panels 2, 2'. As used for the device depicted in FIGS. 1-7, the term barrier refers to a feature that cooperates with at least one other complementary feature of another panel where the panels are in a proximal position relative to each other. As depicted in FIGS. 1-7, the barriers 4, 4' align substantially parallel along the side edges 8, 8', respectively, of the first and second panels 2, 2' in the form of a tongue and groove type barrier. Barrier 4 comprises the tongue barrier as it projects towards the opposing panel 2' when the panels 2, 2' are in a proximal position relative to each other. Barrier 4' comprises the groove barrier as it projects away from the opposing panel 2 when the panels 2, 2' are in a proximal position relative to each other.

Where the device 1 comprises a tongue and groove type barrier, the tongue and groove barrier may comprise a sloped end 16 as depicted in FIGS. 1-7. The sloped end 16 provides clearance between the ends of the barriers 4 and the mating ends of the barriers 4' as the two panels 2, 2' are separated.

Barriers 4, 4' may further comprise draft angles. An exemplary draft angle may range from 0.5 to 2 degrees, although any suitable draft angle may be used. Draft angles may allow the opposing sides of the barrier to engage each other with less friction compared to tongue and groove barriers having no draft angle.

Barriers 4, 4' may be any of any suitable size and shape, and oriented in any suitable position relative to the side edges 8, 8', respectively, of panels 2, 2' to form a pocket area sufficient to receive and contain hair and product as described below. While device 1 depicted in FIGS. 1-7 comprise a plurality of barriers 4, 4', device 1 may comprise only a single barrier.

Alternatively, the barrier 4, 4' may not comprise a projection and/or cavity in relation to the panel but instead comprise an adhesive or magnet. Adhesives may be applied to the interior of panels 2, 2'. Magnetic strips may be applied to the exterior or interior of panels 2, 2'. The one or more magnets may be used to position the panels proximal relative to one another. Barriers, including but not limited to magnets and adhesives, may therefore be separately manufactured and attached or otherwise connected to panels 2, 2'.

The term fastener, as used for purposes of the embodiment of FIGS. 1-7, may refer to a feature that cooperates with at least one other complementary feature to hold the panels in a proximal position relative to each other. As depicted in the embodiment in FIG. 1, the two integrally formed fasteners 5, 5' may take the shape of a button-type closure located at a distal end of panels 2, 2' relative to hinge 3. As disclosed, fasteners 5, 5' may have sufficient friction to hold panels 2, 2' in a proximal position relative to each other.

The fasteners may comprise any suitable shape, size, and/or material. For example, the fasteners may not require projection from the panel but may instead comprise some type of adhesive or magnet. Alternatively, the fasteners may be separately manufactured. Finally, while FIGS. 1-7 depicts the device 1 comprising a plurality of fasteners 5, 5', the device 1 may comprise only one fastener. In a device 1 where barriers may operate similar to fasteners, barrier 4, 4' and fastener 5, 5' as depicted in FIGS. 1-7 may be achieved in device 1 through a single tongue and groove barrier. This single tongue and groove barrier may have sufficient friction to hold panels 2, 2' proximal relative to one another. Alternatively, the barrier and the fastener may be achieved in device 1 through a single fastener.

The barriers 4, 4' may be oriented such that one barrier is oriented substantially parallel along a distal edge of a panel 2, 2' relative to hinge 3, and a second barrier 4, 4' is oriented substantially parallel along a side edge of a panel 2, 2' relative to hinge 3. Device 1 may also comprise hinge 3 positioned parallel along a side edge of the device, not a bottom edge. In such an embodiment, a single barrier 4, 4' may be oriented substantially parallel along the shortest edge of panels 2, 2', any other edge of panels 2, 2', or a combination thereof. One of ordinary skill in the art will readily appreciate that any suitable layout of barriers 4, 4' may be used.

Figure 8:
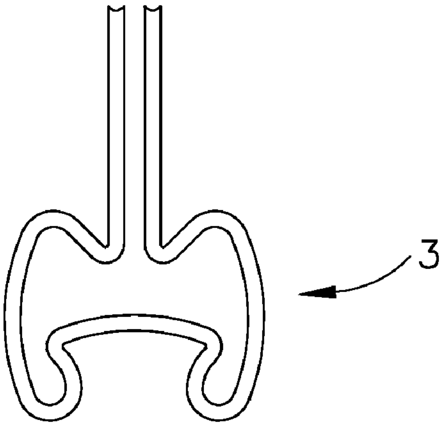
FIG. 8 depicts a side view of the hinge of the device of FIG. 1 in the closed position.
Figure 9:
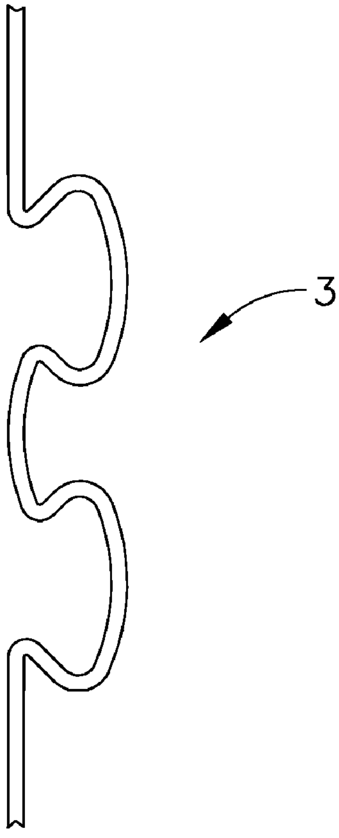
FIG. 9 depicts a side view of the hinge of the device of FIG. 1 in the open position.

As mentioned earlier and as depicted in FIGS. 1-7, hinge 3 connects panels 2, 2' to permit panels 2, 2' to move proximal relative to one another. As depicted, hinge 3 comprises a "W" shaped hinge. FIG. 8 depicts the "W" shaped hinge in a position where panels 2, 2' are proximal relative to one another. FIG. 9 depicts the "W" shaped hinge in a position where panels 2, 2' are not proximal one another. A "W" profile hinge may provide improved length of flexure and hinge life. The "W" profile hinge may also provide and/or allow edges of panels 2, 2' to be brought closer together during use. This action on the part of the hinge may prevent and/or minimize product leakage.

The hinge is not limited to the configuration illustrated in FIGS. 8 and 9, and may have any suitable shape, such as a "V" profile. Alternatively, the hinge may comprise a separate physical component or a simple fold or bend in the plastic. Regardless of the type of hinge, the hinge may be of any appropriate length suitable for operation of the device. For example, the hinge may comprise from about 1-5 inches in length.

Figure 12:
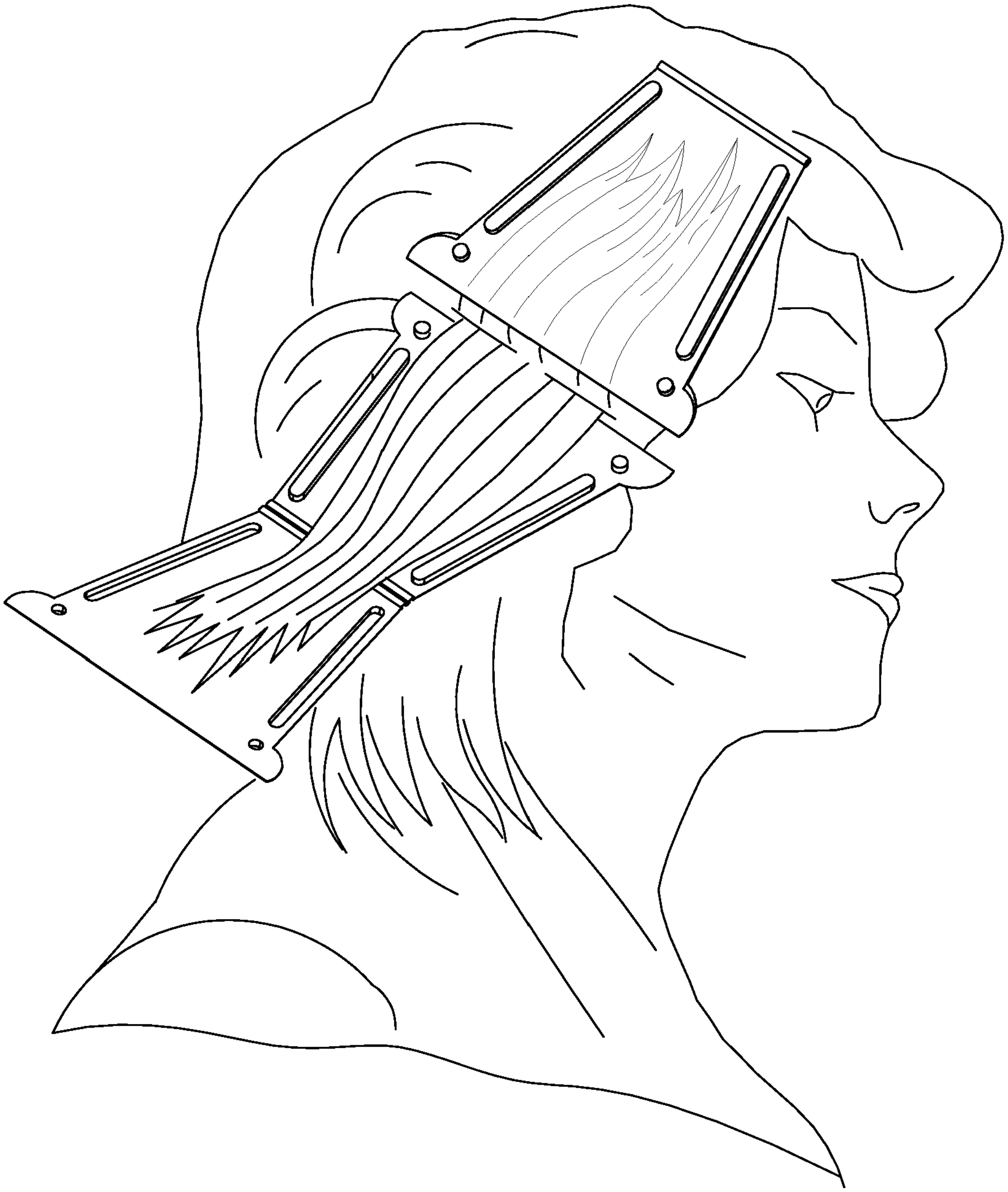
FIG. 12 depicts the device of FIG. 1 in use, and application of the device to the hair.
Figure 13:
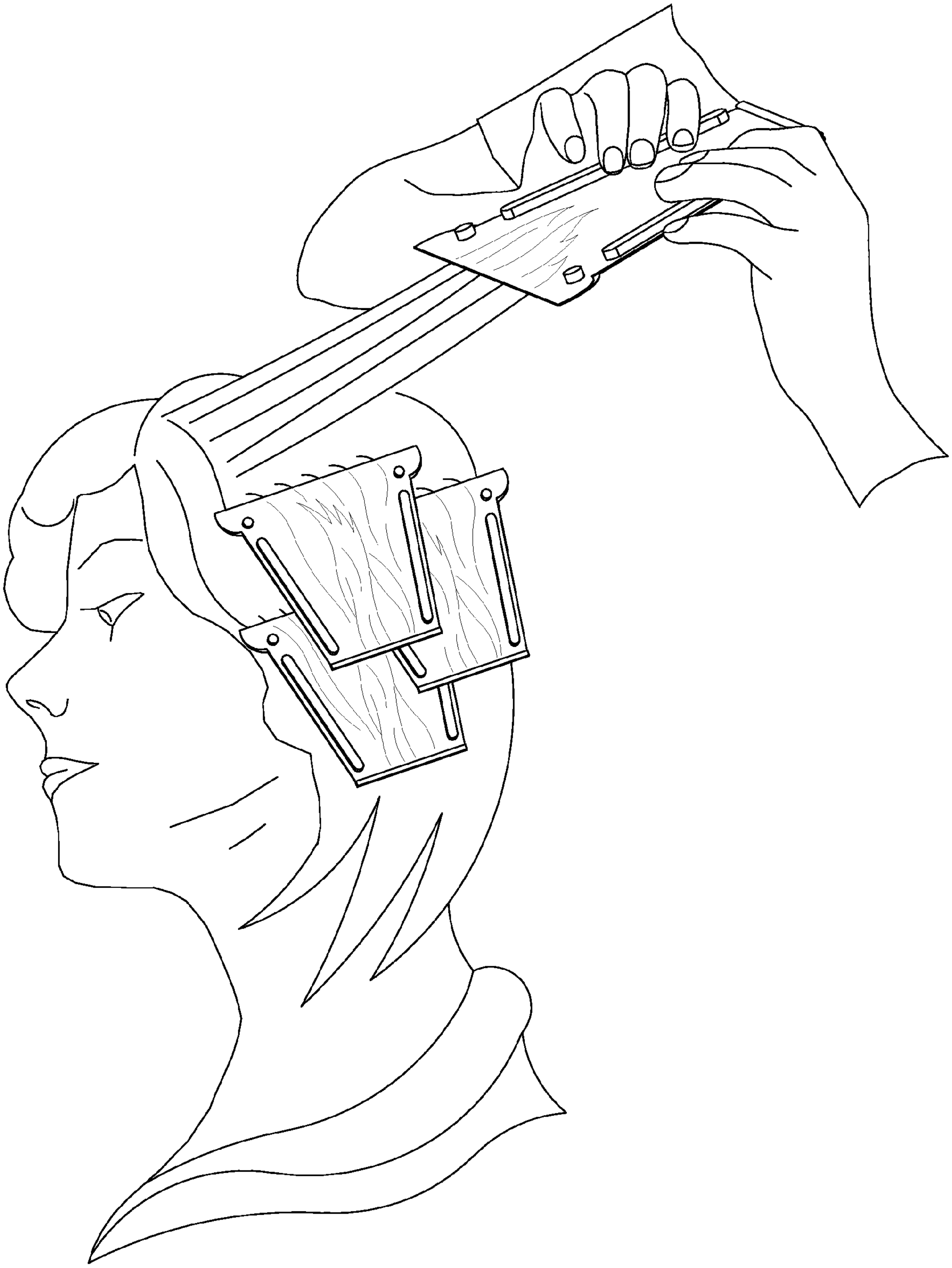
FIG. 13 depicts both the device of FIG. 1 in use, and removal of the device of FIG. 1.

As further depicted in FIGS. 1-7, panels 2, 2' may comprise an edge 6, 6' opposite the hinge 3. As depicted, the wider end or edge 6, 6' may be disposed proximal to the scalp when the device is in use, as can be seen in FIGS. 12 and 13 and described below. As further depicted, panels 2, 2' comprise an end or edge 7, 7' defined by hinge 3 where edge 7, 7' is shorter than edge 6, 6'. The length difference between edge 7, 7' and edge 6, 6' produces a panel 2, 2' having a trapezoidal shape. The trapezoidal shape of panels 2, 2' allows device 1 to accommodate a width of hair adjacent the scalp which can be brought together at its ends.

Figure 4:
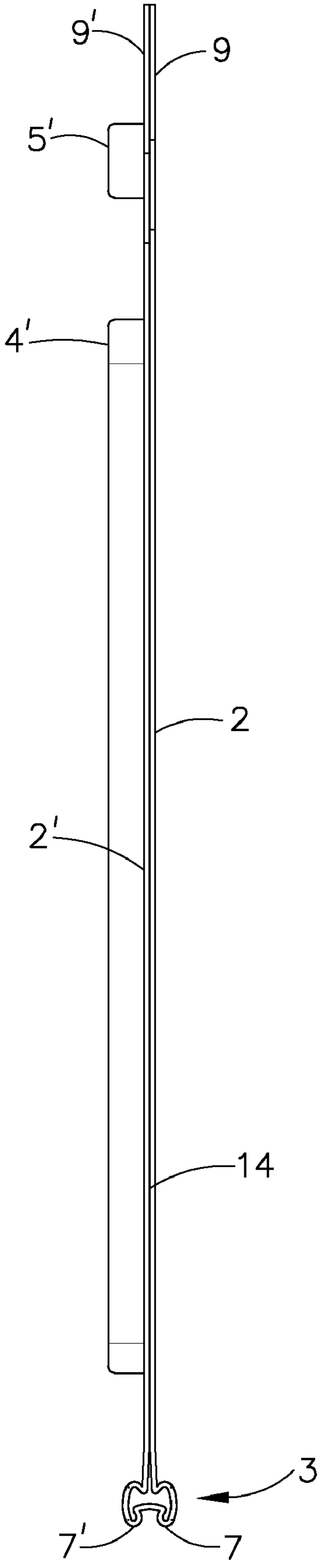
FIG. 4 depicts a side view of the device of FIG. 1 in the closed position.
Figure 5:
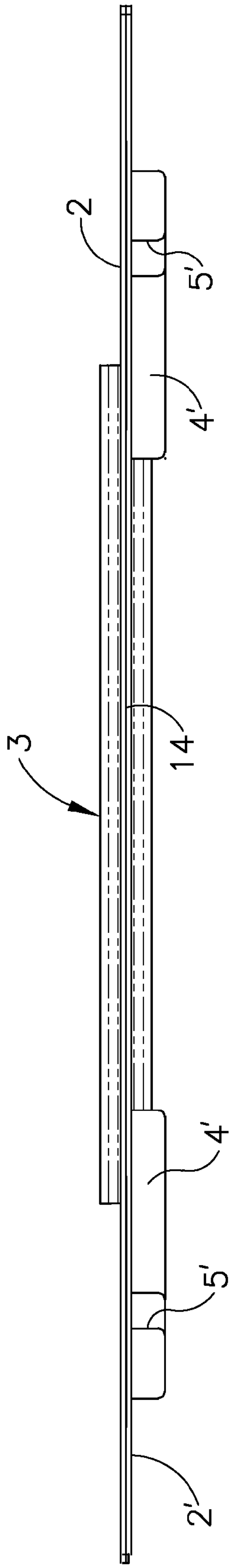
FIG. 5 depicts a side view of the front of the device of FIG. 1 in the closed position.
Figure 6:
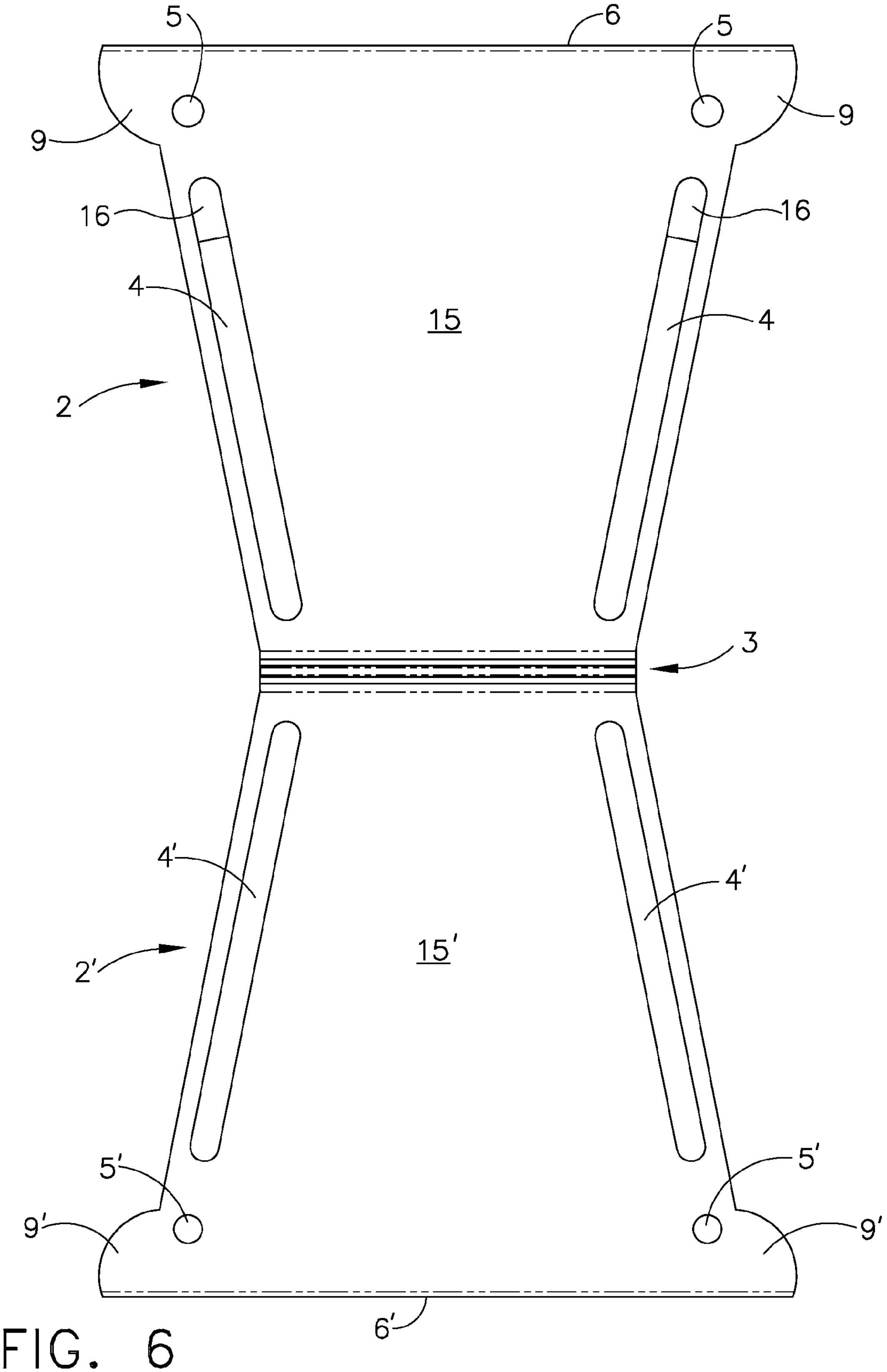
FIG. 6 depicts a top view of the device of FIG. 1 in the open position.
Figure 7:
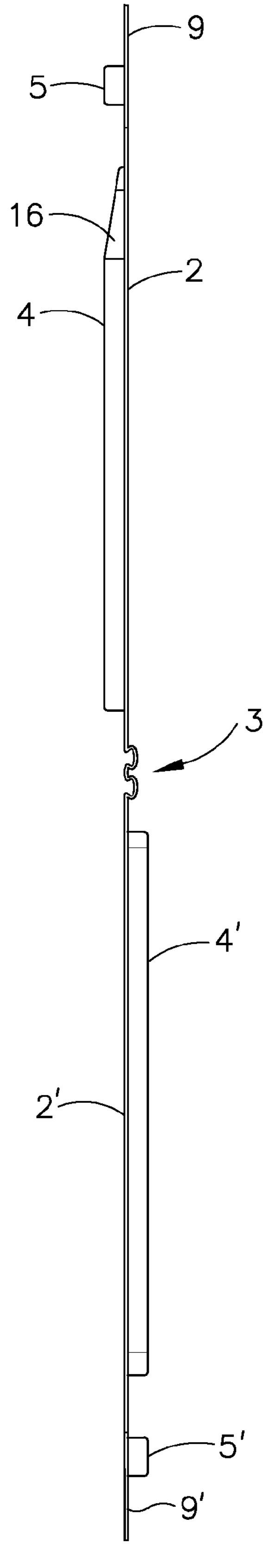
FIG. 7 depicts a side view of the device of FIG. 1 in the open position.

As seen in FIG. 4, where the panels 2, 2' are proximal relative to one another, device 1 comprises a pocket 14 formed between panels 2, 2' when panels 2, 2' are proximal relative to one another. Hair may be disposed in pocket 14. As further depicted, pocket 14 may be configured so that product may not easily escape from device 1 during use. Pocket 14 may not necessarily be hermetically sealed, but rather, device 1 may be sufficiently sealed to enclose the hair with product without significant leakage of the product. However, because a hermetic seal may not necessarily form when the panels are in a proximal position relative to one another, device 1 may not pinch, bend, or crimp the hair at the scalp.

Device 1, as depicted in FIGS. 1-7, may permit full coverage of the entire hair shaft without creating regions that cannot be contacted with the product or creating areas of hair breakage. The device 1 may have sufficient flexibility to allow the hair receiving edges 6, 6' of panels 2, 2' to conform to a variety of head shapes and sizes, automatically forming a curvature where necessary to fit the head shape of the client. Panels 2, 2' may be similarly flexible, such that pocket 14 may be malleable and may conform to the product and hair inside pocket 14. Thus, a functional pocket for holding hair and product may be formed without the need of complex machining or tightly engaged panels that compress the hair. The pocket may form around the section of hair and product, minimizing the presence of trapped air (that can interfere with effective treatment of the hair) while avoiding complex mechanisms or other means to enclose the hair that risk breakage or lines of demarcation. In this device, a close engagement of the first and second panels when proximal one another may be sufficient to prevent leakage of the product.

Figure 2:
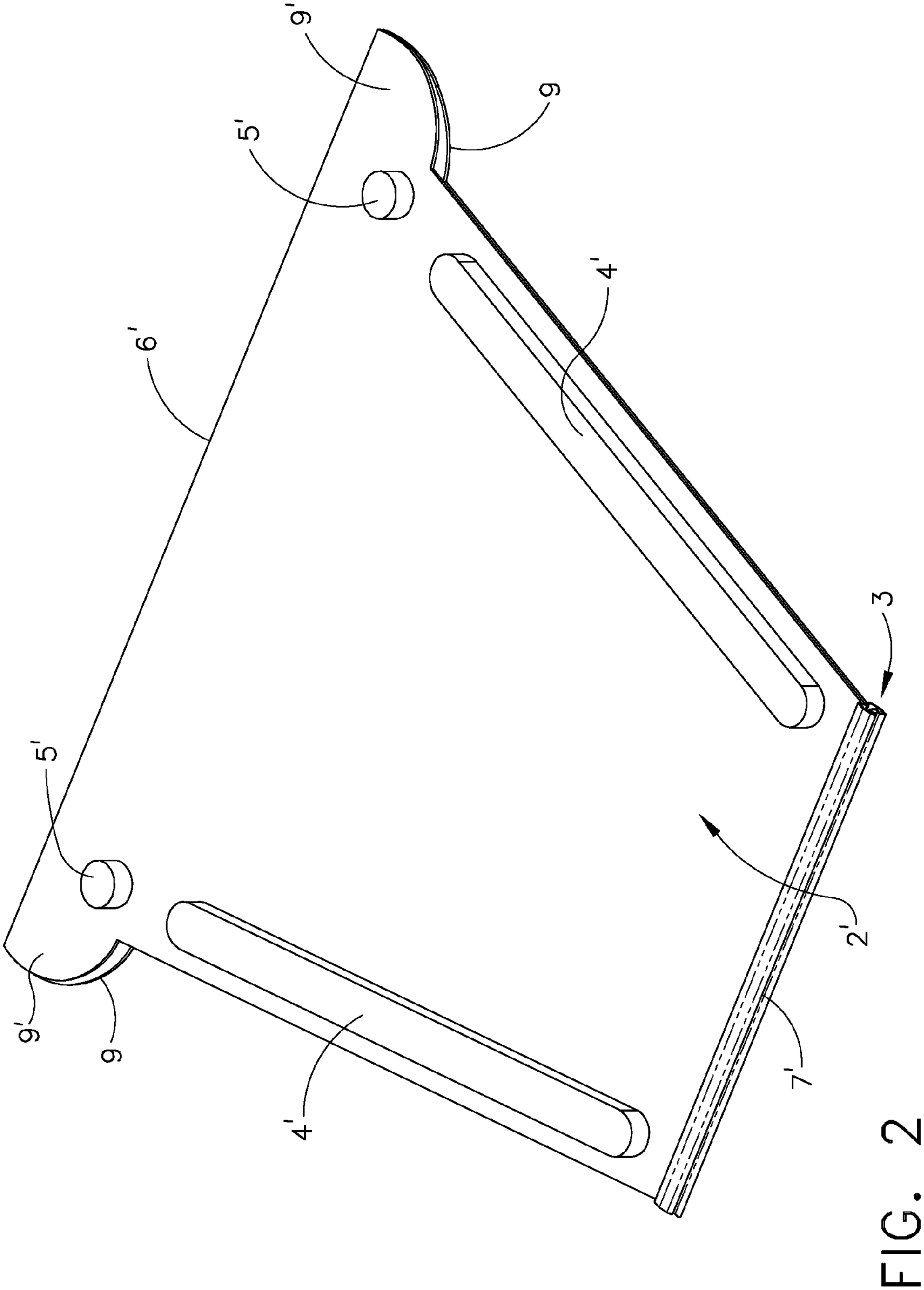
FIG. 2 depicts a perspective view of the device of FIG. 1 in the closed position.
Figure 3:
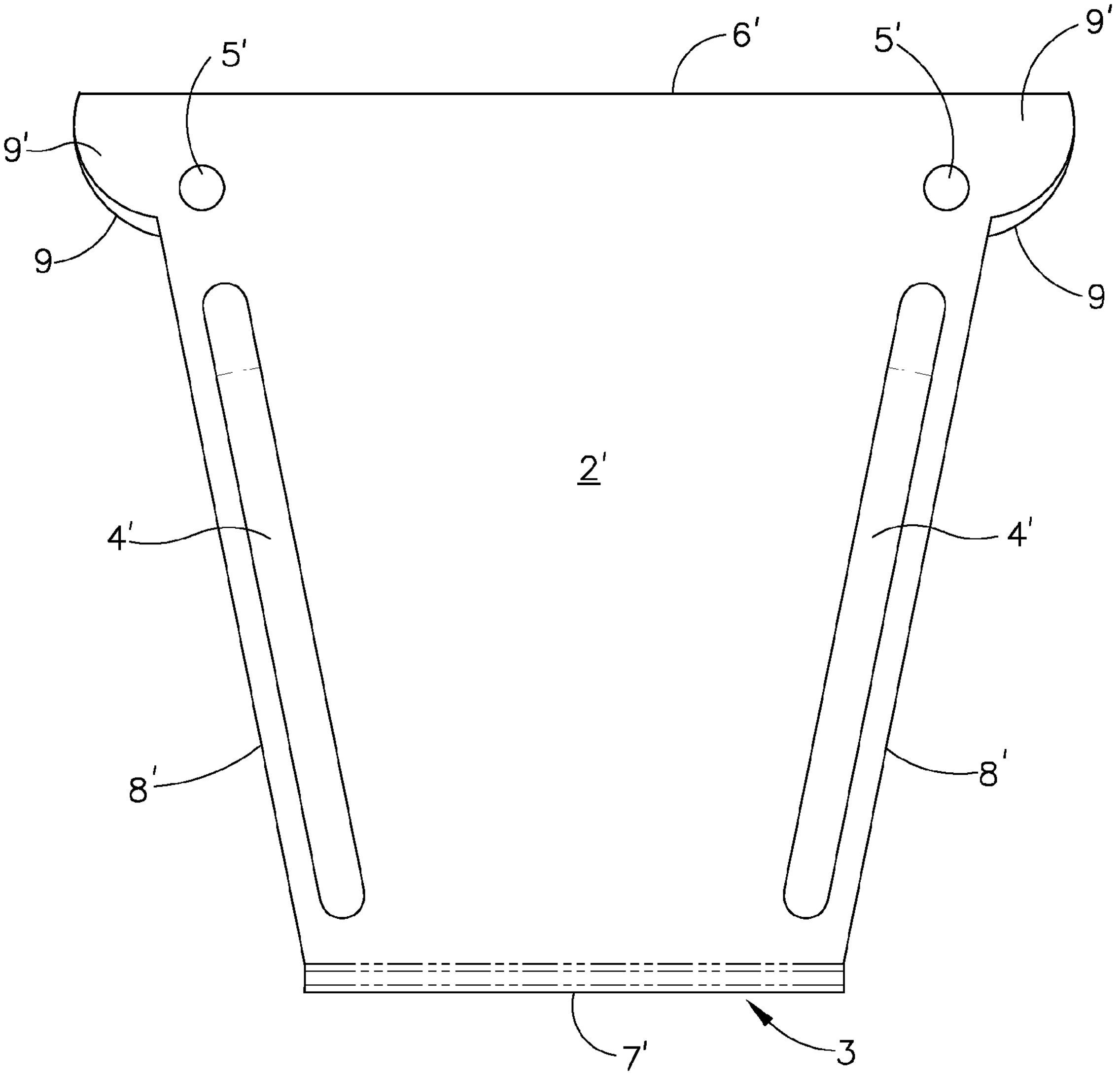
FIG. 3 depicts a top view of the device of FIG. 1 in the closed position.

Device 1 may also comprise one or more releasing features integral with or attached to the first and second panels 2, 2' as seen in FIGS. 1-7. The device 1 may comprise tabs 9, 9' located on the panels 2, 2' respectively as seen in FIG. 2. Tabs 9, 9' have a semi-circular shape and are offset from one another when the first and second panels 2, 2' are proximal relative each other. The tabs may be of any suitable size or shape, or located in any suitable position. Alternatively, device 1 may comprise one side of one panel having a single releasing feature.

Referring to FIGS. 1-13, first and second panels 2, 2' are comprised of a transparent material that allows the chemical processing or treatment of the hair to be viewed through any part of either the first and/or second panel 2, 2' and avoids a need to separate the panels 2, 2' during use to view the process which could interfere with the chemical reaction necessary for successful treatment of hair. Panels 2, 2' need only be transparent to the extent that the user may be able to detect the status of the treatment, particularly where the treatment is coloring or lightening of hair within the device.

While the devices 1 depicted in FIGS. 1-13 are entirely transparent, it should be apparent to one of skill in the art that the device 1 may be configured in other ways without departing from the scope and spirit of the present invention. For example, panels 2, 2' may comprise both non-transparent and transparent portions. It is advisable, but not required, that at least some portion of the panel is transparent for viewing the hair and product. Alternatively, only one panel may be transparent or have a transparent portion.

Device 1 may be comprised of any suitable material. The material should be sufficiently resistant to the chemical treatment or products used with the embodiment. For example, the material may include, but is not limited to, synthetic plastics such as polyethylene, polyvinylchloride, polystyrene, and copolymers of polyvinylchloride with polyvinyl acetate. The material may be sufficiently resistant to the chemicals to be used more than once.

Figure 10:
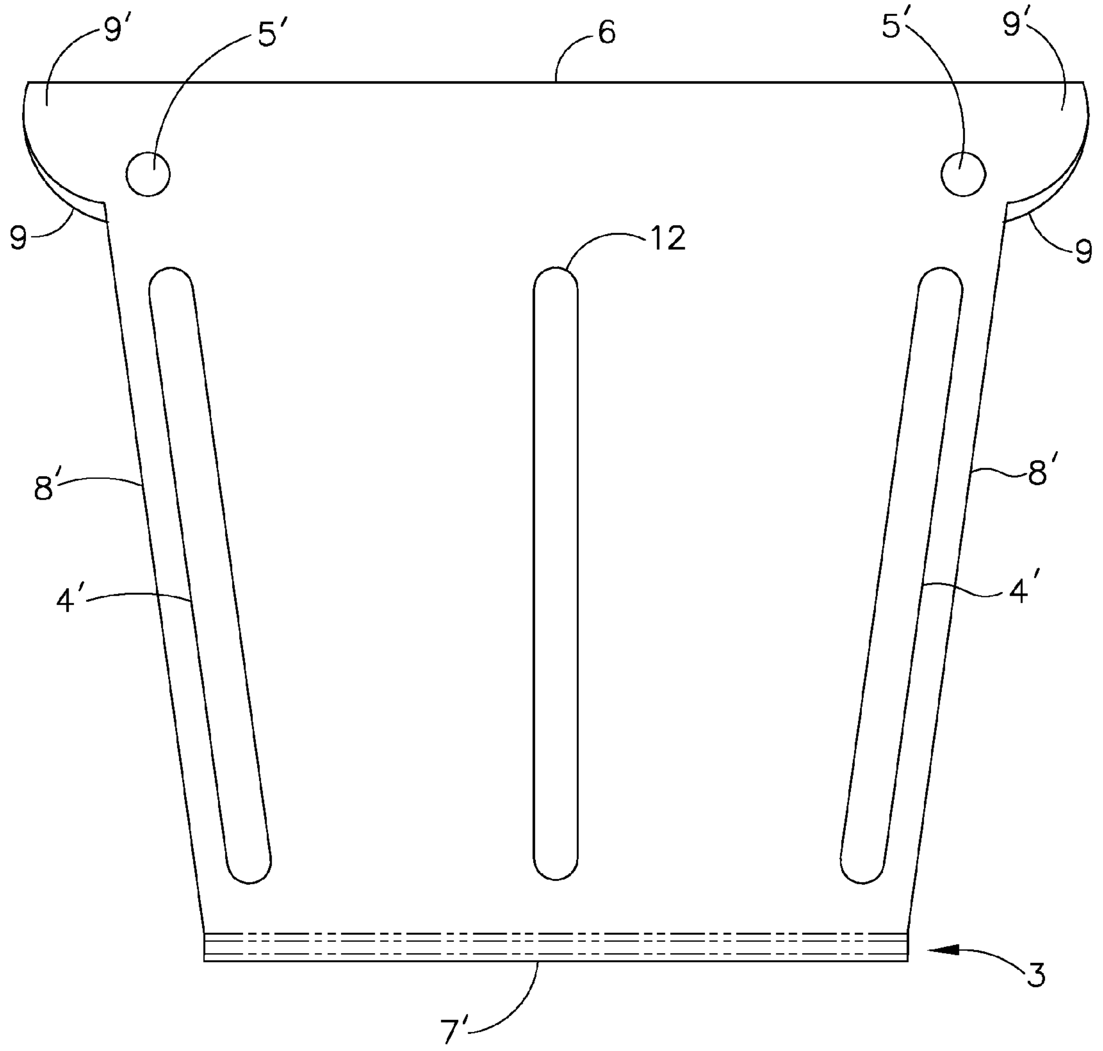
FIG. 10 depicts an alternative embodiment of the device having two compartments.
Figure 11:
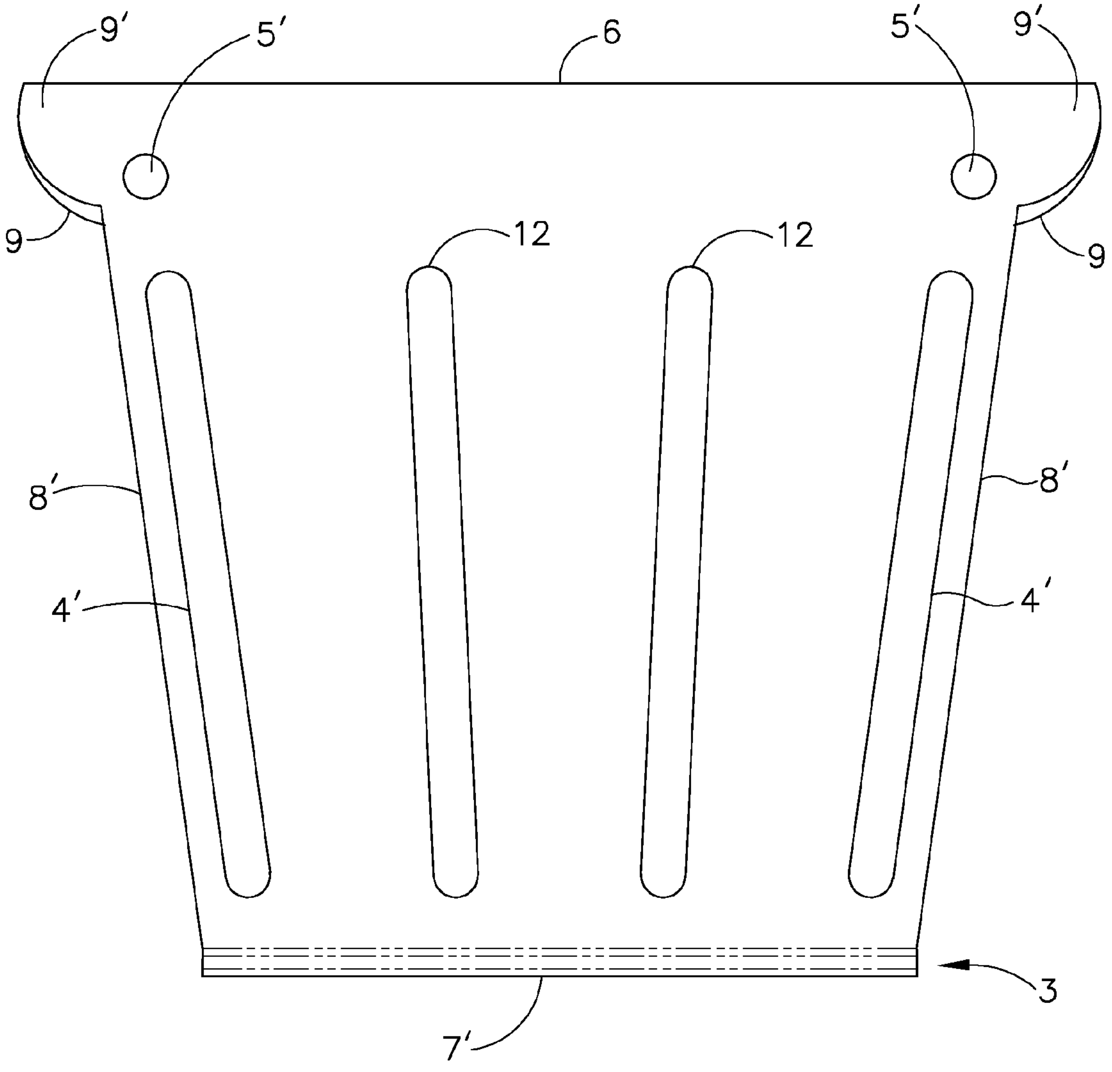
FIG. 11 depicts an alternative embodiment of the device having three compartments.

FIGS. 10 and 11 depict multiple embodiments. As depicted in FIG. 10, device 1 comprises at least one divider 12. Divider 12 defines at least two receiving wells. The receiving wells may permit a plurality of hair sections to be treated. FIG. 11 depicts device 1 comprising two dividers 12 that in combination help define at least three receiving wells. Multiple receiving wells may be defined by dividers 12 to create multiple sections of hair, apply multiple and/or distinct products to each section of hair, and/or avoid unwanted mixing or intermingling of multiple treatments. Dividers 12 may be in the form of a tongue and groove as illustrated in FIGS. 10 and 11, with the tongue configuration being on panel 2 and the grove configuration being on panel 2'.

The devices depicted in FIGS. 10 and 11 may be used in conjunction with specially designed bowls and brushes (not shown) configured to complement the variously sized and compartmentalized devices. For example, the embodiment of the device depicted in FIG. 10 having two receiving areas, may be used with a similarly sized bowl having similarly spaced compartments. For example, a bowl having three compartments each having a width of one inch may be used in conjunction with an embodiment of the device having three receiving areas where each area may have a width of one inch.

Yet further, a brush (not shown) may be provided which is complementary to the bowl and an embodiment of the device. The brush may have a space between the bristles of the brush sufficient to prevent mixing of the multiple chemical treatments contained within the bowls and applied to the hair. In use, the brush may be designed to accommodate the bowl. The brush may accommodate the bowl by having separated bristles such that the brush may be inserted into the bowl to contact the contents of the multiple compartments of the bowl without contacting the divider. A brush user may then efficiently and easily apply multiple colors or products to sections of hair that are placed in the multiple receiving areas of this embodiment of the device without using multiple bowls or brushes.

In another example, a bowl (not shown) having three compartments of 1.5 inch widths may be used with an embodiment of a hair treatment device having a plurality of receiving wells wherein the width of each receiving well may be 1.5 inches. The two compartments of the bowl may be partially filled two different products. Each compartment of the bowl may have a different product. The stylist then may section, for example, a 5-inch section of hair, which may be further divided into 2.5 inch sections. Each of the 2.5 inch sections may be placed in respective receiving areas on the device.

Upon sectioning the hair, a brush (not shown) having a width of approximately 3.5 inches may be used. The bristles of the brush may have a space of approximately 0.5 to 0.75 inches. The remaining bristles of the brush may be comprised of two sections of approximately 1.5 inches in width, such that each section may be placed in a compartment of the bowl without interference with the bowl divider. The brush may be placed into the bowl for a sufficient length of time to allow the bristles to be saturated with a sufficient amount of product. The brush may then be applied to the hair where one product is applied to one 2.5 inch section of the hair and a second product may be applied to the other 2.5 inch section of the hair. As such, multiple brushes and bowls may not be required to apply multiple products to hair using the multi-compartment device.

As shown in the embodiments of FIGS. 1-13, the device may be stackable, whether in the open or proximal position, for both storage and shipping of the device.

The device depicted in FIGS. 1-7 may further relate to a method of chemically treating the hair. One method for which the device may be used to chemically treat hair comprises the steps of selecting a portion of the hair, disposing the section of the hair in a receiving well, applying chemical product to the section of hair, and forming a pocket surrounding the section of hair by placing the panels 2, 2' proximal to each other. This process may be followed for each device used on the hair. Upon each use of a device, the chemical treatment process continues for an amount of time sufficient to permit a desired result. When so desired or needed, each device may be slidably removed from each hair section such that the hair section is no longer encompassed by the device. Once the reaction is deemed complete by the stylist, the devices may be removed individually or collectively by sliding the closed device from the strands of hair. Thus, the device may be slidably removed without opening the device, improving the efficiency of use. Yet further, multiple devices may be removed at once.

Another method, for using the device 1 having at least one divider, as depicted in FIG. 11, comprises placing panel 2 under a section of hair such that barriers 4, 4' contain hair in separate receiving wells defined by dividers 12. After placing a section of hair on panel 2, the hair is sectioned into a plurality of receiving wells. After sectioning the hair into different receiving wells, product is applied to the respective hair sections. After applying product to the respective hair sections, panels 2, 2' are moved in a proximal position relative to each other allowing the hair product to work. Upon permitting the hair product to work completely, device 1 may be removed. In one method, device 1 may be removed by sliding.

The instant invention also relates to a kit for chemically treating hair. The kit may include at least one device as described above; at least one tray or bowl for holding product; and at least one brush suited to fit the tray or bowl. The kit may further optionally comprise product for the treatment of hair, or other accessories convenient to the methods described herein or known in the art.

The foregoing description of an embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims submitted herewith.

What is claimed is:

1. A device for chemically treating hair with a product comprising:

(a) a first panel comprising a distal end and a proximal end;

(b) a second panel comprising a distal end and a proximal end;

(c) at least one hinge connecting the proximal end of the first panel and the proximal end of the second panel;

(d) a plurality of barriers wherein at least one barrier on the first panel cooperates with at least one barrier on the second panel to secure the first panel and the second panel proximal each other;

(e) said first and second panels forming a pocket therebetween when said first and second panels are disposed proximal one another, said pocket having an open edge configured to receive hair therethrough, said open edge not comprising a barrier; and (f) one or more dividers disposed within said pocket, said pocket being defined into two or more receiving wells by said one or more dividers, each of said two or more receiving wells having a open edge defined by said open edge of said pocket.

2. The device of claim 1 wherein the plurality of barriers comprise at least one tongue barrier and at least one groove barrier.

3. The device of claim 2 wherein said at least one tongue barrier comprises a sloped end.

4. The device of claim 1 wherein at least one panel is transparent.

5. The device of claim 1 wherein the plurality of barriers are positioned on edges of the first panel and edges of the second panel each extending between the respective distal ends of the panels and the respective proximal ends of the panels.

6. The device of claim 1 wherein the first panel further comprises at least one receiving well defined by a plurality of barriers positioned on the first panel.

7. The device of claim 1 wherein the hinge is a “W” shaped hinge.

8. The device of claim 1 further comprising a plurality of fasteners wherein at least one fastener is positioned on the distal end of the first panel to cooperate with at least one fastener on the distal end of the second panel to secure the first panel and the second panel proximal each other.

9. The device of claim 8 wherein the plurality of fasteners that cooperate with each other to secure the panels proximal one another comprise a button-type element and a receiving element.

10. The device of claim 1 wherein at least one of said first and second panels comprises a tab on the distal end of that panel.

11. The device of claim 10 wherein the tab comprises a semi-circular shape.

12. A device for chemically treating hair with more than one product comprising:

(a) a first panel comprising at least one edge and a plurality of barriers;

(b) a second panel comprising at least one edge and a plurality of barriers;

(c) at least one hinge connecting the first and the second panel;

(d) said first and second panels forming a pocket therebetween when said first and second panels are disposed proximal one another, said pocket having an open edge configured to receive hair therethrough, said open edge not comprising a barrier; and (f) one or more dividers disposed within said pocket, said pocket being defined into two or more receiving wells by said one or more dividers, each of said two or more receiving wells having a open edge defined by said open edge of said pocket.

13. A device according to claim 12 wherein each of said one or more dividers comprise a tongue and groove.

14. A device according to claim 12 wherein the first panel further comprises a tab.

15. The device of claim 1 wherein said open edge comprises said distal end of said first panel and said distal end of said second panel.

16. The device of claim 1, wherein said pocket does not have any barriers disposed generally parallel to said open edge.

17. The device of claim 12, wherein said open edge is generally parallel to said at least one hinge, wherein said edges extend between said open edge and said at least one hinge, and wherein said pocket does not have any barriers disposed transverse to said plurality of barriers of said first panel or to said plurality of barriers of said second panel.

* * * * *